United States Patent [19]
Weirich

[11] Patent Number: 5,695,324
[45] Date of Patent: Dec. 9, 1997

[54] BODY CONFORMING COMPOUND SANITARY NAPKIN

[75] Inventor: David Michael Weirich, West Chester, Ohio

[73] Assignee: The Procter & Gamble Company, Cincinnati, Ohio

[21] Appl. No.: 681,781

[22] Filed: Jul. 29, 1996

Related U.S. Application Data

[63] Continuation of Ser. No. 399,324, Mar. 6, 1995, abandoned.

[51] Int. Cl.[6] .................... A61F 13/15; A61F 13/20
[52] U.S. Cl. .................... 604/378; 604/385.1; 604/387; 604/400
[58] Field of Search .................... 604/378, 379, 604/382, 385.1, 386, 387, 393, 400

[56] References Cited

U.S. PATENT DOCUMENTS

| | | | |
|---|---|---|---|
| D. 342,785 | 12/1993 | Farrell | D24/125 |
| 2,043,325 | 6/1936 | Jackson, Jr. | 128/284 |
| 2,295,016 | 9/1942 | Scribner | 128/290 |
| 2,331,355 | 10/1943 | Strongson | 128/290 |
| 2,662,527 | 12/1953 | Jacks | 128/290 |
| 2,683,457 | 7/1954 | Cunningham | 128/290 |
| 2,917,049 | 12/1959 | Delaney | 128/285 |
| 2,929,379 | 3/1960 | Poulsen | 128/290 |
| 2,965,102 | 12/1960 | Harwood | 128/290 |
| 3,183,909 | 5/1965 | Roehr | 128/290 |
| 3,406,689 | 10/1968 | Hicks et al. | 128/290 |
| 3,512,530 | 5/1970 | Jones, Sr. | 128/290 |
| 3,528,422 | 9/1970 | Hodas | 128/290 |
| 3,570,492 | 3/1971 | Bettencourt | 128/290 |
| 3,737,931 | 6/1973 | Glassman | 128/290 R |
| 3,805,790 | 4/1974 | Kaczmarzyk et al. | 604/378 |
| 4,022,210 | 5/1977 | Glassman | 128/284 |
| 4,046,147 | 9/1977 | Berg | 128/290 R |
| 4,340,058 | 7/1982 | Pierce et al. | 128/287 |
| 4,425,130 | 1/1984 | DesMarais | 604/389 |

(List continued on next page.)

FOREIGN PATENT DOCUMENTS

| | | |
|---|---|---|
| 0 405 403 A2 | 2/1991 | European Pat. Off. . |
| 0 426 197 A2 | 5/1991 | European Pat. Off. . |
| 0 525 778 A3 | 2/1993 | European Pat. Off. . |
| 0 685 212 A2 | 12/1995 | European Pat. Off. . |
| 2 653 328 | 4/1991 | France . |
| 2 029 766 | 6/1970 | Germany . |
| 5-28327 | 4/1993 | Japan . |
| 5-115506 | 5/1993 | Japan . |
| 5-33721 | 5/1993 | Japan . |
| 2 191 098 | 12/1987 | United Kingdom . |
| 2 232 600 | 12/1990 | United Kingdom . |

(List continued on next page.)

OTHER PUBLICATIONS

U.S. Patent Application Serial No. 08/225,191 (P&G Case 5208), filed Apr. 8, 1994, in the names of McFall, et al. entitled Sanitary Napkin Having an Independently Displaceable Central Core Segment.

(List continued on next page.)

*Primary Examiner*—John G. Weiss
*Assistant Examiner*—Ki Yong O.
*Attorney, Agent, or Firm*—David M. Weirich; Steven W. Miller; Jacobus C. Rasser

[57] ABSTRACT

The present invention pertains to a compound sanitary napkin. The compound sanitary napkin comprises a primary absorbent member including an absorbent core and an outer cover. The primary absorbent member has a second portion and an first portion; the first portion being vertically opposed to the second portion. The width of the first portion is greater than the width of the second portion. The compound sanitary napkin further comprises a secondary absorbent member that is joined with the primary absorbent member juxtaposed the second portion. The secondary absorbent member preferably comprises a liquid impervious backsheet and an absorbent material joined thereto. Optionally, the secondary absorbent member includes a backsheet, a topsheet joined to the backsheet and an absorbent core disposed between the backsheet and the top sheet.

19 Claims, 3 Drawing Sheets

U.S. PATENT DOCUMENTS

| | | | |
|---|---|---|---|
| 4,490,147 | 12/1984 | Pierce et al. | 604/378 |
| 4,578,069 | 3/1986 | Whitehead et al. | 604/370 |
| 4,589,876 | 5/1986 | Van Tilburg | 604/385 R |
| 4,627,848 | 12/1986 | Lassen et al. | 604/378 |
| 4,758,240 | 7/1988 | Glassman | 604/379 |
| 4,781,711 | 11/1988 | Houghton et al. | 604/378 |
| 4,848,572 | 7/1989 | Herrera | 206/440 |
| 4,938,756 | 7/1990 | Salek | 604/368 |
| 4,963,139 | 10/1990 | Dabroski | 604/378 |
| 5,030,229 | 7/1991 | Yang | 604/378 |
| 5,057,096 | 10/1991 | Faglione | 604/385.1 |
| 5,092,860 | 3/1992 | Pigneul | 604/380 |
| 5,169,394 | 12/1992 | Jean | 604/385.1 |
| 5,171,302 | 12/1992 | Buell | 604/385.1 |
| 5,267,992 | 12/1993 | Van Tilburg | 604/387 |
| 5,324,278 | 6/1994 | Visscher et al. | 604/385.1 |
| 5,336,208 | 8/1994 | Rosenbluth et al. | 604/329 |
| 5,342,337 | 8/1994 | Runeman et al. | 604/378 |
| 5,364,382 | 11/1994 | Latimer et al. | 604/378 |
| 5,391,160 | 2/1995 | Runeman et al. | 604/378 |
| 5,507,735 | 4/1996 | Van Iten et al. | 604/385.1 |

FOREIGN PATENT DOCUMENTS

| | | |
|---|---|---|
| WO 92/07535 | 5/1992 | WIPO . |
| WO 94/16658 | 8/1994 | WIPO . |
| WO 95/16422 | 6/1995 | WIPO . |
| WO 95/29655 | 11/1995 | WIPO . |
| WO 96/19170 | 6/1996 | WIPO . |

OTHER PUBLICATIONS

U.S. Patent Application Serial No. 08/294,662 (P&G Case 5395), filed Aug. 19, 1994, in the names of Mayer, et al., entitled Body Fitting Compound Sanitary Napkin.

U.S. Patent Application Serial No. not yet assigned (P&G Case 5591), filed Feb. 24, 1995, in the names of David Christopher Oetjen, et al., Compound Sanitary Napkin.

U.S. Patent Application Serial No. not yet assigned (P&G Case 5599), filed Mar. 2, 1995, in the names of John L. Hammons, et al., entitled Anatomical Compound Sanitary Napkin.

BODY CONFORMING COMPOUND SANITARY NAPKIN

This application is a continuation of application Ser. No. 08/399,324, filed Mar. 6, 1995, which has been abandoned.

FIELD OF THE INVENTION

The present invention relates to disposable sanitary napkins. As used herein, sanitary napkins are considered to be absorbent devices designed to be worn externally of the body by women, usually during their menstrual periods, and to receive and contain menses and other vaginal discharges. Disposable sanitary napkins are intended to be discarded after use and soiling rather than being cleaned and reused.

BACKGROUND OF THE INVENTION

In their simplest form, disposable sanitary napkins comprise an absorbent element (sometimes referred to as an absorbent core) interposed between a liquid pervious body-contacting element (sometimes referred to as a topsheet or an overwrap) and a liquid impervious protective barrier (sometimes referred to as a backsheet). The absorbent element is intended to receive and contain menses and other vaginal discharges. The body-contacting element is intended to provide more or less comfortable and dry-feeling contact with body surfaces while allowing free passage of fluids therethrough into the absorbent element. The protective barrier is intended to prevent menses or other vaginal discharges which are expelled or which escape from the absorbent element from soiling the user's garments.

In addition to the three functional elements mentioned above, disposable sanitary napkins are generally provided with means for supporting the device adjacent the user's crotch area, even as the user moves, where it can most effectively perform its intended function. Typically, sanitary napkins are provided with an adhesive attachment means for securing the device to the inner crotch area of the user's undergarments.

While previously known sanitary napkins do perform their intended function, each conventional design suffers from certain deficiencies in one or more of absorbency of body fluids, protection of the user's garments from soiling, and/or physical comfort to the user.

With respect to disposable sanitary napkins, at least two general classes presently exist. One such class is identified as being intended for the absorption of medium to high menstrual flows. These sanitary napkins offer a relatively high absorptive capacity. Absorptive capacity is commonly achieved by providing the sanitary napkin with a relatively thick and bulky absorbent member. While having a relatively high absorptive capacity, the bulkiness of the absorbent member may cause a certain degree of wearing discomfort.

A second class of sanitary napkins are intended for light or low menstrual flows and are commonly referred to as pantiliners or pantishields. Sanitary napkins of this class, as a group, are thinner, somewhat more flexible and generally more comfortable than those of the first class. However, sanitary napkins of the second class typically lack the absorptive capacity of sanitary napkins of the first class.

One attempt to provide the benefits of the previously described two classes of sanitary napkins into a single compound sanitary napkin is disclosed in commonly assigned U.S. Pat. No. 4,425,130 issued to DesMarais on Jan. 10, 1984. The compound sanitary napkin of DesMarais comprises a primary menstrual pad and a panty protector joined to one another at their corresponding ends in such a manner that the two constituents are free to move relative to one another along essentially their entire common length. The primary menstrual pad is intended to absorb the bulk of the bodily fluids discharged by the user, while the panty protector is intended to protect the user's garments from soiling. In use, the relative freedom of movement between the primary menstrual pad and the panty protector serves to maintain the primary menstrual pad adjacent the user's crotch region while the panty protector remains associated with the user's undergarment. While the relative freedom of movement between the primary menstrual pad and the panty protector serves to maintain the primary menstrual pad near the user's crotch region, this freedom of movement may lead to a lack of stability if the primary menstrual pad moves laterally beyond the side edges of the panty protector, providing an opportunity for soiling the user's undergarment.

Furthermore, the relative freedom of movement between the primary menstrual pad and the panty protector alone may be insufficient to capture bodily fluid as it exits the wearer's vaginal opening. The primary menstrual pad is preferably narrow enough to at least reside partially within the external genitalia. Optionally, the primary menstrual pad may be wider than the distance between the labia majora, but exhibits a lateral compression or conformability at relatively low forces, such as the forces exerted by the soft tissue of the female external genitalia, such that a portion of the primary menstrual pad is able to at least reside partially within the external female genitalia. By being conformable at relatively low forces, the primary absorbent member remains comfortable during use. In addition, the primary menstrual pad preferably exhibits a resilient recovery to enable the pad to conform to the body as the pad and body interface is subjected to shape changes.

As the primary menstrual pad is made narrower to fit the body, the panty protector preferably remains sufficiently wide enough to provide a stable attachment to the wearer's undergarment and to sufficiently cover the undergarment to protect it from soiling.

SUMMARY OF THE INVENTION

The present invention pertains to a compound sanitary napkin. The compound sanitary napkin comprises a primary absorbent member including an absorbent core and an outer cover. The primary absorbent member has a first portion and a second portion; the first portion being vertically opposed to the second portion. The width of the first portion is greater than the width of the second portion. The compound sanitary napkin further comprises a secondary absorbent member that is joined with the primary absorbent member juxtaposed the second portion. The secondary absorbent member preferably comprises a liquid impervious backsheet and an absorbent material joined thereto. Optionally, the secondary absorbent member comprises a backsheet, a topsheet joined to the backsheet and an absorbent core disposed between the backsheet and the topsheet.

BRIEF DESCRIPTION OF THE DRAWINGS

While the specification concludes with claims particularly pointing out and distinctly claiming the present invention, it is believed that the present invention will be better understood from the following description in conjunction with the following drawings, in which like reference numbers identify identical elements and wherein:

DETAILED DESCRIPTION OF THE INVENTION

This invention is of a body fitting compound sanitary napkin which exhibits absorbency for bodily fluids, the protection of the user's garments from soiling, and physical comfort to the user. The term "sanitary napkin", as used herein, refers to an article which is worn by females adjacent to the pudendal region and which is intended to absorb and contain the various exudates which are discharged from the body (e.g., blood, menses, and urine) and which is intended to be discarded after a single use (i.e., it is not intended to be laundered or otherwise restored or reused). The term "compound sanitary napkin", as used herein, refers to a sanitary napkin comprised of separate constituents joined to one another to form a unitary structure. Interlabial devices which reside partially within and partially external of the wearer's vestibule are also within the scope of this invention. As used herein, the term "pudendal" refers to the externally visible female genitalia and is limited to the labia majora, the labia minora, the clitoris, and the vestibule.

Figure 1:
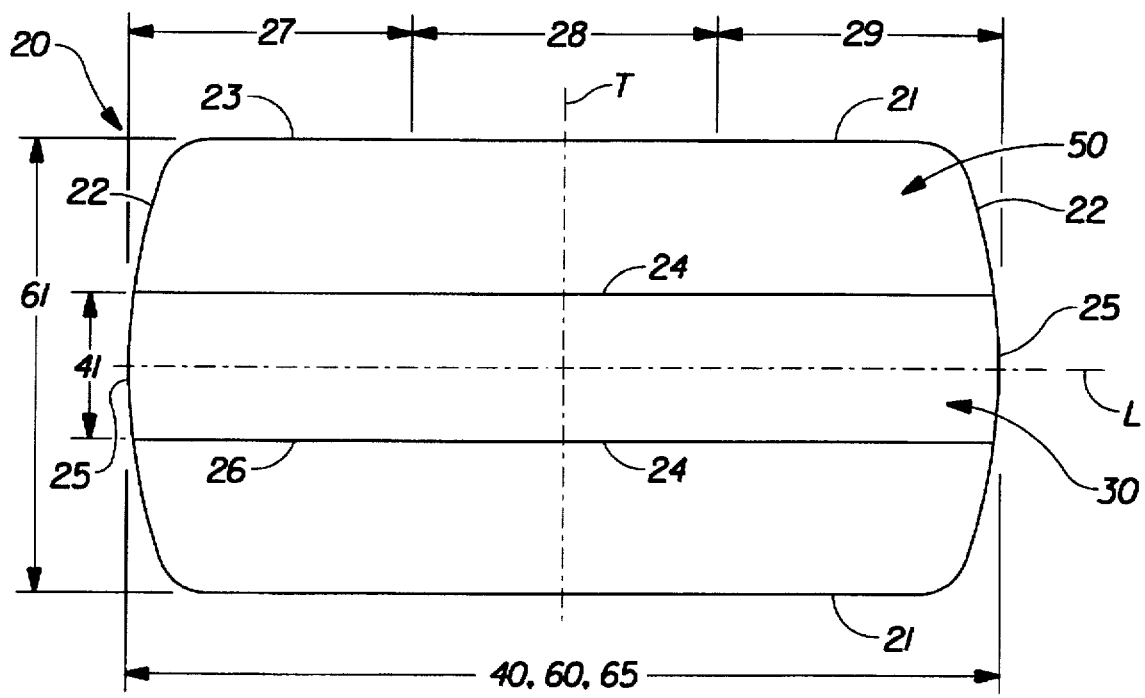
FIG. 1 is a top plan view of one embodiment of the compound sanitary napkin of the present invention.
Figure 2:
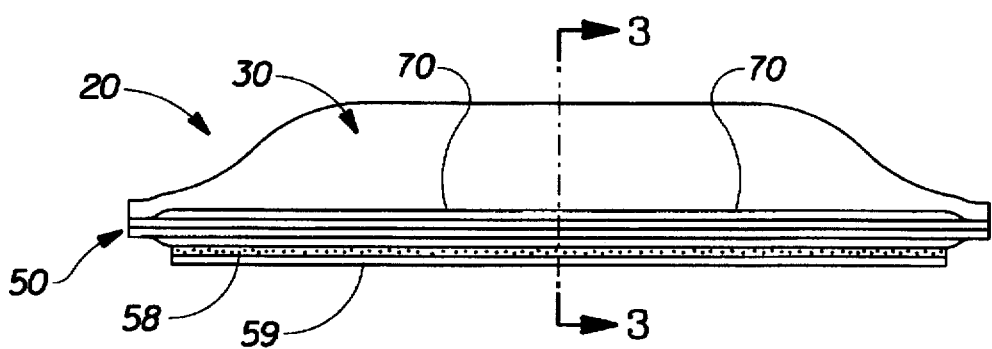
FIG. 2 is a side elevation view of the compound sanitary napkin shown in FIG. 1.
Figure 3:
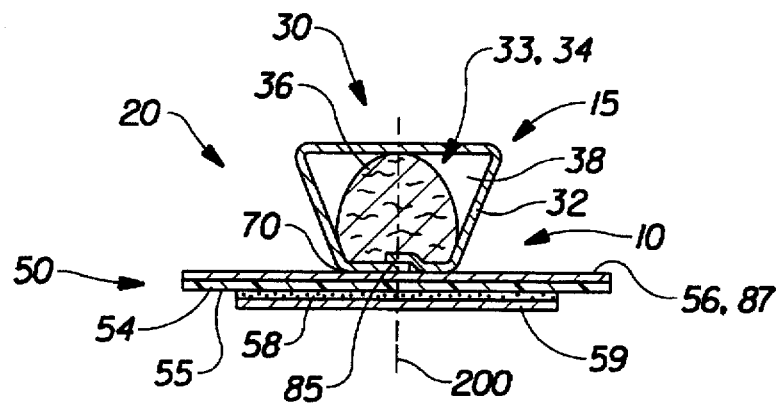
FIGS. 3 and 3A are cross-sectional views of the compound sanitary napkin shown in FIGS. 1 and 2 as taken along section line 3—3 of FIG. 2.

FIGS. 1–3 show one preferred embodiment of a compound sanitary napkin 20 of the present invention. As can be seen in FIGS. 1–3, the compound sanitary napkin 20 comprises a primary absorbent member 30 and a secondary absorbent member 50 joined together by union means 70. The compound sanitary napkin has two surfaces, a body contacting or facing surface 40, and a garment facing or contacting surface 55. The primary and secondary absorbent members each have corresponding body facing and garment facing surfaces. The garment facing surface 55 of the primary absorbent member 30 may be referred to as the secondary absorbent member facing side 41. The body facing surface of the secondary absorbent member 30 may be referred to as the primary absorbent member facing side 43. The compound sanitary napkin 20 has a longitudinal centerline L and a transverse centerline T. The term "longitudinal", as use herein, refers to a line, axis or direction in the plane of the compound sanitary napkin that is generally aligned with (e.g., approximately parallel to) a vertical plane which bisects a standing wearer into left and right body halves when the compound sanitary napkin is worn. The terms "transverse" or "lateral", as used herein, are interchangeable, and refer, to a line, axis, or direction which lies within the plane of the compound sanitary napkin that is generally perpendicular to the longitudinal direction.

The primary absorbent member 30 has side edges 24 and end edges 25 which together form the periphery 26 of the primary absorbent member 30. The secondary absorbent member 50 has longitudinal 14 extending side edges 21 and end edges 22 which together form the periphery 23 of the secondary absorbent member and the compound sanitary napkin 20. The compound sanitary napkin 20 has a first end region 27, a central region 28, and a second end region 29.

The primary absorbent member 30 is that constituent of the compound sanitary napkin 20 intended to absorb the bulk of bodily fluids discharged by the user. The primary absorbent member 30 comprises an absorbent means 33, such as absorbent core 34, and an outer cover 32 superimposed on the absorbent core 34. (As used herein, the term "superimposed" means adjacent or juxtaposed, but not necessarily in contact with or joined to.) The entire outer cover 32 may be liquid pervious, however, other embodiments are contemplated wherein portions of the outer cover 32 are liquid impervious or hydrophobic.

Figure 3A:
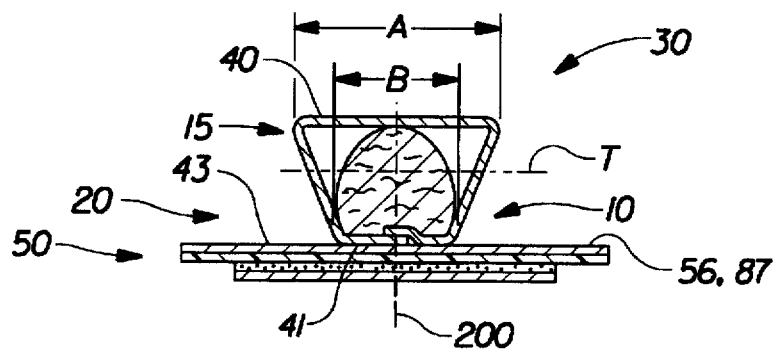

As shown in FIGS. 3 and 3A, the primary absorbent member 30 has a vertical centerline 200, a second portion 10 such as secondary absorbent member facing side 41, having a width B and an first portion 15 such as body facing side 40, which is vertically opposed to the second portion 10, the first portion 15 having a width A. (The widths A and B of the first portion 15 and the second portion 10, respectively, of a preferred compound sanitary napkin are best shown in FIG. 3A.) The second portion 10 is that portion of the primary absorbent member 30 juxtaposed the body facing surface 87 of the secondary absorbent member 50. The first portion 15 is that portion of the primary absorbent member 30 vertically opposed to the second portion 10 which comprises the portion of the primary absorbent member 30 having the greatest width A. (The "width" at any given location is determined by measuring the lateral or transverse dimension at that location. Thus, a measurement is taken generally perpendicular to the vertical centerline 200 and generally parallel to the transverse centerline T.) The first portion 15 and the second portion 10 can take on any shape or width, so long as the width A of the first portion 15 is greater than the width B of the second portion 10.

Preferably, the outer cover 32 is compliant, soft feeling, and non-irritating to the wearer's skin. Further, at least a portion of the outer cover 32 is liquid pervious, permitting liquid to readily penetrate through its thickness. A suitable outer cover 32 may be manufactured from a wide range of materials such as woven and nonwoven materials; polymeric materials such as apertured formed thermoplastic films, apertured plastic films, and hydroformed thermoplastic films; porous foams; reticulated foams; reticulated thermoplastic films; and thermoplastic scrims. Suitable woven and nonwoven materials can be comprised of natural fibers (e.g., wood or cotton fibers), synthetic fibers (e.g., polymeric fibers such as polyester, polypropylene, or polyethylene fibers); or from a combination of natural and synthetic fibers.

The outer cover 32 may be a unitary member or may be comprised of two or more elements joined together to form the outer cover 32. Further, any portion of the materials comprising the outer cover 32 may be coated, laminated, treated or otherwise manipulated to impart or enhance any desired characteristics such as strength, flexibility, liquid perviousness or imperviousness.

A preferred outer cover 32 comprises formed film having apertures. Apertured formed films are preferred for the outer cover 32 because they are generally pervious to body exudates and yet non-absorbent, thus reducing the likelihood of liquids passing back through the film and rewetting the wearer's skin. Accordingly, the surface of the formed film which is in contact with the body remains dry, thereby reducing body soiling and creating a more comfortable feel for the wearer. Further formed films are easily manufactured with non-apertured portions that provide liquid impervious areas that prevent any fluids from passing therethrough. Suitable formed films are described in U.S. Pat. No. 3,929,135, issued to Thompson on Dec. 30, 1975; U.S. Pat. No.

4,324,246, issued to Mullane, et al. on Apr. 13, 1982; U.S. Pat. No. 4,342,314, issued to Radel, et al. on Aug. 3, 1982; U.S. Pat. No. 4,463,045, issued to Ahr, et al. on Jul. 31, 1984; and U.S. Pat. No. 5,006,394, issued to Baird on Apr. 9, 1991. Each of these patents are incorporated herein by reference. One especially preferred outer cover 32 for the primary absorbent member 30 of the present invention comprises a formed film described in one or more of the above patents and marketed on sanitary napkins by The Procter & Gamble Company of Cincinnati, Ohio as "DRI-WEAVE".

In a preferred embodiment of the present invention, the body facing surface of at least a portion of the outer cover 32 is hydrophilic so as to help liquid transfer through the outer cover 32 faster than if the body facing surface was not hydrophilic. This diminishes the likelihood that menstrual fluid will flow off the outer cover 32 rather than flowing into and being absorbed by the absorbent core 34. In a preferred embodiment, surfactant is incorporated into the polymeric materials of the formed film such as is described in U.S. patent application Ser. No. 08/072,660, entitled "Absorbent Article Having a Nonwoven and Apertured Film Coversheet" filed on Jun. 4, 1993 by Aziz, et al., which is incorporated herein by reference. Alternatively, the body facing surface of the outer cover 32 can be made hydrophilic by treating it with a surfactant such as described in U.S. Pat. No. 4,950,264 issued to Osborn on Aug. 21, 1990 and which is incorporated herein by reference.

As stated above, the outer cover 32 is preferably superimposed on the absorbent core 34. To insure proper fluid transfer between the outer cover 32 and the absorbent core 34 it is preferred that the outer cover be substantially continuously joined to the underlying absorbent core 34 throughout their common association or interface. (As used herein, the term "joined" encompasses configurations whereby an element is directly secured to another element by affixing the element to the other element, as well as configurations whereby an element is indirectly secured to another element by affixing the element to an intermediate member or members which in turn are affixed to the other element.) By substantially continuously joining the outer cover 32 to the underlying absorbent core 34 the outer cover 32 will have a reduced tendency to separate from the absorbent core 34 during use. Separation of the absorbent core from the outer cover 32 may inhibit fluid transfer from the outer cover 32 into the underlying absorbent core 34. The outer cover 32 may be joined to the absorbent core 34 by any suitable means, including, but not limited to joining the outer cover 32 with the absorbent core 34 with adhesives such as by spray-gluing or applying lines or spots of adhesives between the outer cover 32 and the absorbent core 34. Alternatively, or additionally, the outer cover 32 may be joined with the absorbent core 34 simply by wrapping the outer cover 32 about the absorbent core 34, by entangling the fibers of the absorbent core 34 with the outer cover 32, by fusing the outer cover 32 to the absorbent core 34 with a plurality of discrete individual fusion bonds, or by any other means known in the art.

Referring now to FIG. 3, it can be seen that outer cover 32 may completely wrap the absorbent core 34 of the primary absorbent member 30. The outer cover 32 is shown in FIG. 3 to have a seam 85 adjacent the secondary absorbent member 50. Although such a configuration is advantageous to keep the seam 85 away from any body contact, the figure is not meant to limit the scope of the invention. Other suitable embodiments are contemplated wherein the seam 85 is disposed in any location about the absorbent core. Further, any number of seams, folds, pleats or bonds in the outer cover 32 are acceptable so long as the primary absorbent member 30 is able to function to absorb and contain bodily fluids while being comfortable to wear. The outer cover 32 of the primary absorbent member 30 is shown in FIG. 3 to be a separate and distinct element from the topsheet 52 of the secondary absorbent member 50. In such embodiments, the outer cover 32 is preferably joined to the topsheet 52 of the secondary absorbent member 50 by union means 70.

Figure 5:
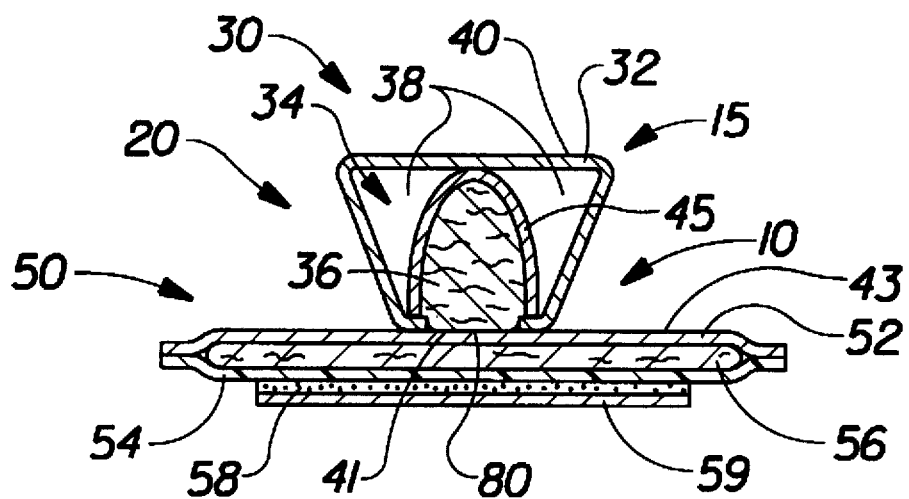
FIGS. 5 and 6 are cross-sectional views of alternative embodiments of the compound sanitary napkin of the present invention.

In another embodiment, as shown in FIG. 5, the outer cover 32 does not completely encircle the absorbent core 34 of the primary absorbent member 30. Rather, the outer cover 32 substantially encircles the absorbent core 34. (As used herein, the term "substantially encircle" means that the outer cover overlays more than half of the absorbent core, and more preferably most of the absorbent core.) Because the outer cover 32 does not completely encircle the absorbent core 34, a channel 80 is formed. The channel 80 provides a means for any liquid not retained by the primary absorbent member 30 to be deposited onto the topsheet 52, the absorbent element 56 or any other element of the secondary absorbent member 50 such that it may be absorbed and contained therein. (An alternative embodiment of the present invention comprising a channel 80 is shown in FIG. 5.)

Figure 6:
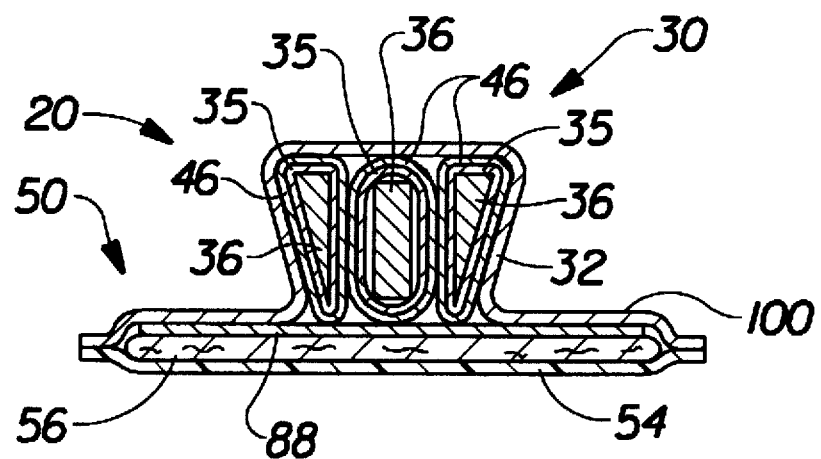

Optionally, as shown in FIG. 6, the outer cover 32 of the primary absorbent member 30 and the topsheet 52 of the secondary absorbent member 50 may comprise a single web of material, such as web 100. In such embodiments web 100 substantially encircles the absorbent core 34 of the primary absorbent member 30 and extends outwardly therefrom to cover at least a portion of the secondary absorbent member 50. Suitable materials for use as the web 100 are described above with regard to the outer cover 32 of the primary absorbent member and the topsheet 52 of the secondary absorbent member 50. Although the web 100, as shown in FIG. 6 may cover the entire body facing surface of the second absorbent member 50, it need not do so. Further, the exact configuration of the web 100 may vary so long as it substantially encircles the absorbent core 34 of the primary absorbent member 30.

In the embodiment of FIG. 6 the web 100 serves as a union means connecting the primary absorbent member 30 and the secondary absorbent member together. The compound sanitary napkin may also include additional union means to connect the primary absorbent member 30 to the secondary absorbent member. Suitable additional union means include but are not limited to adhesives, fusion bonds or any other union means described herein.

Figure 4:
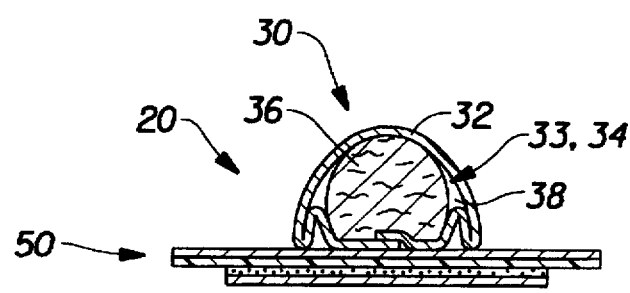
FIG. 4 is a cross-sectional view of the compound sanitary napkin shown in FIG. 1 after it has been placed into position on the wearer.

The absorbent core 34 of the present invention primarily functions to absorb and maintain bodily exudates. However, in many embodiments, the absorbent core 34 functions as a shaping member to maintain the shape of the primary absorbent member 30. Thus, it may be desirable for the primary absorbent member 30 to comprise an absorbent core including more than one core members, such as first core member 36 and second core member 38 shown in FIG. 3. (As used herein, the term "core members" is used to describe different elements comprised in the absorbent core 34 or different regions within the absorbent core 34 that may perform different functions.) The absorbent core 34 may comprise any number of first core members 36 and/or second core members 38. Preferably, the first core member(s) 36 will be sufficiently resilient to provide the primary absorbent member 30 with intimate contact with the exposed genitalia of the female user. Intimate contact with the exposed female genitalia helps provide better fluid transfer from the user into the primary absorbent member 30 without allowing fluid to bypass and/or run-off the primary absorbent member 30. Further, it is important that the first absorbent member(s) 36 be sufficiently resilient such that when subjected to normal wearing forces the secondary absorbent member 30 does not permanently collapse. While the resilient characteristics of the absorbent core 34 allow for improved fit, they must be balanced against the need for the product to be both soft and comfortable for the wearer. Thus, materials selected for use as the second core member (s) 38 are preferably compliant, soft, comfortable, and compressible under relatively small forces to enhance the body fit and comfort of the primary absorbent member 30. In addition to being compressible, the materials comprising the second absorbent member(s) 38 are preferably conformable such that the primary absorbent member 30 is able to provide improved fit into and around the labia and perineum. (An example of the compound sanitary napkin 20 of FIGS. 3 and 3A after it has been worn is shown in FIG. 4.)

As shown in FIGS. 3 and 5, preferred embodiments of the present invention comprises an absorbent core 34 having a first core member 36 of generally arcuate cross-section. The first core members 36 are preferably elongate, having a dimension in the direction of the length of the sanitary napkin 20. The first core member(s) 36, however, may comprise a wide variety of shapes such as rectangular, oval, trapezoidal, pentagonal, U-shaped, Z-folded, and still provide the primary absorbent member 30 with an first portion width A greater than the second portion width B.

In FIG. 6, the core 34 comprises a plurality of first core members 36 that provide the preferred body fitting shape of the primary absorbent member 30. In one preferred embodiment, as shown in FIG. 6, at least one of the first core members 36 is in the shape of an elongated parallelepiped. However, the shape, size, number and arrangement of the first core members 36 may vary so long as the primary absorbent member 30 may be provided with an first portion width A greater than the second portion width B. Further, the first core members 36 may comprise any material as described herein with regard to the absorbent core, the absorbent layer, the acquisition layer or any other absorbent material as is known in the art.

In a preferred embodiment, the first core members 36 are wrapped in a containment layer 35. The containment layer 35 may comprise any material that will absorb and contain fluids, including, but not limited to those described herein with respect to absorbent cores and acquisition layers. An especially preferred containment layer 35 comprises thermally bonded air laid, as described above, and in U.S. patent application Ser. No. 08/141,156. Further, the first core members 36 are preferably wrapped in an acquisition layer 46. The acquisition layer 46 may comprise any of the materials as further described hereinbelow with regard to acquisition layers. A particularly preferred acquisition layer 46 comprises a nonwoven web, such as the nonwoven web available from Fiberweb Noah America under the trade designation P-9. As shown in FIG. 6, the outer cover 32 is superimposed over the arrangement of first core members 36 to form the primary absorbent member 30 of the present invention. Examples of other suitable core member materials, shapes, sizes and arrangements are described in further detail in U.S. Pat. Nos. 4,340,058 entitled "Sanitary Napkin" issued to Pierce et al., on Jul. 20, 1982 (describing elongate absorbent pads with generally circular cross-sections); and 4,490,147 entitled "Absorbent Sanitary Napkin" issued to Pierce et at., on Dec. 25, 1984; each of which is incorporated by reference herein.

The absorbent core 34 may be any absorbent means which is generally compressible, conformable, resilient, non-irritating to the wearer's skin and capable of absorbing and containing body exudates. Preferably, the total absorbent capacity of the absorbent core 34 should be compatible with the intended exudate loading for the primary absorbent member 30 of the compound sanitary napkin 20. Further, the absorbent capacity of the absorbent core 34 may be varied to accommodate wearers ranging in the expected amount of exudate fluid volume. For instance, a different absorbent capacity may be utilized for compound sanitary napkins intended for day time use as compared with those intended for night time use, or for compound sanitary napkins intended for use by teenage females as compared with those intended by more mature women.

The absorbent core 34 may be manufactured from a wide variety of liquid absorbent materials commonly used in disposable sanitary napkins, and other disposable absorbent articles. Further, the first core member(s) 36 may comprise the same or different materials than the second core member (s) 38. Examples of suitable absorbent materials include comminuted wood pulp, which is generally referred to as airfelt; creped cellulose wadding, modified cross-linked cellulose fibers such as those described in U.S. Pat. No. 5,217,445 issued to Young, et al. on Jun. 8, 1993; capillary channel fibers (fibers having intra-fiber capillary channels such as those described in U.S. Pat. No. 5,200,248 issued to Thompson, et al. on Apr. 6, 1993); absorbent foams such as those described in U.S. Pat. No. 5,260,345, issued to DesMarais, et al. on Nov. 9, 1993; U.S. Pat. No. 5,268,244 issued to DesMarais, et al. on Dec. 7, 1993; U.S. Pat. No. 5,331,015 issued to DesMarais et al., on Jul. 19, 1994; and U.S. Pat. No. 5,387,207 issued to Dyer et al., on Feb. 7, 1995); thermally bonded air laid materials such as those material described in U.S. patent application Ser. No. 08/141,156, entitled "Catamenial Absorbent Structures Having Thermally Bonded Layers For Improved Handling of Menstrual Fluids and Their Use In Catamenial Pads Having Improved Fit and Comfort" filed in the name of Richards, et al. on Oct. 21, 1993 (P&G Case 5051); polyurethane, absorbent sponges; synthetic staple fibers; polymeric fibers; hydrogel-forming polymer gelling agents; peat moss; glass fibers or any equivalent materials or combinations of materials. All of the above-identified Patents and patent applications are hereby incorporated by reference herein.

One suitable first core member 36 comprises polyurethane foam available from Foamex under the trade designation Foamex 08-8982. Other suitable absorbent cores comprising foams are described in U.S. Pat. No. 5,260,345 issued Nov. 9, 1993; U.S. Pat. No. 5,147,345 issued Sep. 15, 1992; and U.S. Pat. No. 5,149,720 issued Sep. 22, 1992. The first and third patents listed in the names of DesMarais, et al., and the second patent issued in the name of Young, et al. Additional cores comprising foams are described in European Application 0 293 208 B1. Absorbent cores comprising sponges are described in U.S. Pat. Nos. 3,512,530; and 3,954,493; and French Patent 2,203,827. Examples of alternative suitable absorbent cores are described in detail in co-pending U.S. patent application Ser. No. 08/277,733 (P&G Case 5395). All of the above-identified references are hereby incorporated by reference herein.

The primary absorbent member 30 may further comprise a resilient member 45 as is illustrated in FIG. 5. The resilient member 45 may comprise a single member or a plurality of individual members. Suitable materials which may be used as the resilient member 45 include, but are not limited to nylon, polypropylene, polyurethane, polyethylene, polyester, synthetic rubber, glass fibers and other synthetic materials such as formed films, or natural materials such as rubber, sponges, and the like or any suitable material which is capable of resisting collapse under normal wearing conditions of sanitary napkins during use. One preferred resilient member comprises polyurethane foam available from Foamex under the trade designation Foamex 08-8982. The resilient member 45 may be manufactured in a wide variety of shapes such as arcuate, rectangular, triangular, oval, square, pentagonal, U-shaped, Z-folded or any other shape as is known in the art.

The resilient member 45 may extend throughout the entire length of the primary absorbent member 30. The resilient member 45 may only extend through a portion of the length of the primary absorbent member 30. The resilient member 45 may be positioned within the first end region 27, the central region 28, the second end region 29 or any combination of the above. For example, the resilient member 45 may be positioned in either the first end region 27 or the second end region 29 of the primary absorbent member 30, in both the first end region 27 and the second end region 29 of the primary absorbent member 30, in the central region 28 of the primary absorbent member 30, or in the central region 28 and the end regions 27 and 29 of the primary absorbent member 30. The resiliency of the resilient member 45 is preferably not affected by the presence of body exudates absorbed by and contained within the absorbent core. The sustained resiliency of the resilient member 45 permits the primary absorbent member 30 to maintain intimate contact with the body of the wearer during use. The primary absorbent member 30 may include a resilient member 45 similar to the internal shaping component disclosed in U.S. patent application Ser. No. 08/225,441, (P&G Case 5109R), entitled "Sanitary Napkin having an Internal Shaping Component", filed Apr. 8, 1994, in the name of Carl L. Bergman. The disclosure of the above referenced application is incorporated herein by reference.

The primary absorbent member 30 may comprise an acquisition layer 46, as shown in FIG. 6, positioned between the outer cover 32 and the absorbent core 34. The acquisition layer 46 may serve several functions including improving wicking of exudates over and into the absorbent core 34. By improving the wicking of exudates, the acquisition layer 46 provides a more even distribution of the exudates throughout the absorbent core 34. The acquisition layer 46 may be comprised of several different materials including nonwoven or woven webs of synthetic fibers including polyester, polypropylene, or polyethylene; natural fibers including cotton or cellulose; blends of such fibers; or any equivalent materials or combinations of materials. Examples of sanitary napkins having an acquisition layer are more fully described in U.S. Pat. No. 4,950,264 issued to Osborn and U.S. patent application Ser. No. 07/944,764, "Absorbent Article Having Fused Layers", filed Oct. 7, 1992 in the names of Cree, et al. Each of these references is incorporated herein by reference. In a preferred embodiment, the acquisition layer 46 may be joined with the outer cover 32 by any of the conventional means for joining webs together, most preferably by fusion bonds as is more fully described in the above-referenced Cree application.

While the primary absorbent member 30 can be generally of any cross-sectional shape in its unstressed condition, the first portion 15 has a width A greater than the width B of the second portion 10. The length 40 and the width 41 of the primary absorbent member 30 can be of any convenient dimension. The primary absorbent member 30, is preferably from about 2 to 35 cm long, more preferably from about 10 to 35 cm long, and most preferably from about 20 to 35 cm long. A particularly preferred primary absorbent member 30 has a length of about 24 cm. The primary absorbent member 30, is preferably from about 0.5 to 5 cm wide, more preferably from about 0.5 to about 4 cm wide, and most preferably from about 0.5 to about 3 cm wide.

It may be desirable to provide a compound sanitary napkin having a primary absorbent member with varying degrees of width or caliper throughout its length. For example, the primary absorbent member 30 may be relatively thicker in the central region 28 as opposed to the end regions 27 and 29. Alternatively, the primary absorbent member may be relatively thinner in the central region 28 as opposed to the end regions 27 and 29.

The second constituent of the compound sanitary napkin 20 of the present invention is the secondary absorbent member 50. The secondary absorbent member can be of generally rectangular shape. However, other suitable shapes include but are not limited to oval, hourglass, dog-bone, asymmetric and other shapes that are known in the art. Further, the secondary absorbent member 50 of the present invention is preferably relatively thin and flexible. The secondary absorbent member 50 preferably has a caliper of less than about 3.0 millimeters, more preferably less than about 2.6 millimeters, even more preferably less than about 2.2 millimeters, and most preferably less than about 2.0 millimeters.

The secondary absorbent member 50 preferably comprises an absorbent element 56 and a liquid impervious backsheet 54 joined with the absorbent element 56. As shown in FIG. 3, the absorbent element 56 may form the body contacting surface 87 of the secondary absorbent member 50. In other preferred embodiments, as shown in FIGS. 5 and 6, the secondary absorbent member 50 comprises a liquid impervious backsheet 54, a liquid pervious topsheet 52 joined with the backsheet 54 and an absorbent element 56 positioned between the topsheet 52 and the backsheet 54. In yet other embodiments, as shown in FIG. 6, the secondary absorbent member 50 may comprise an acquisition layer 88 in addition to or in place of the topsheet 52.

The topsheet 52 can be any fluid pervious material commonly used in sanitary napkins, disposable diapers, and the like. The topsheet 52 can be any of the materials described above as being useful in the outer cover 32 of the primary absorbent member 30, including, but not limited to nonwovens or apertured formed films.

The acquisition layer 88 of the secondary absorbent member 50 may comprise any of the materials described above with regard to the primary absorbent member's 30 acquisition layer 46. In preferred embodiments, the secondary absorbent member 50 comprises an acquisition layer 88 disposed between the topsheet 52 and the absorbent element 56 as shown in FIG. 6. However, embodiments are contemplated wherein the acquisition layer 88 replaces the topsheet 52, the absorbent element 56 or both. In such configurations, the acquisition layer 88 provides any absorption characteristics desired in the secondary absorbent member 50.

The absorbent element 56 of the secondary absorbent member 50 primarily functions to protect the user's garments from soiling by absorbed fluids which may be expelled from the primary absorbent member 30 or which may inadvertently bypass the primary absorbent member 30. Thus, the absorbent element 56 of the secondary absorbent member 50 generally performs a different function from that of the absorbent core 34 and is preferably somewhat thinner and less bulky than the absorbent core 34. The absorbent element 56 may comprise any of the materials described above as being useful in the absorbent core 34 or the acquisition layers 46 and 88. However, paper tissue (either single or multiple plies) is also suitable for use in the absorbent element 56. In one preferred embodiment, the absorbent element 56 is formed of from about 1 to about 5 plies of paper tissue.

Paper tissue comprising one or more plies having a basis weight of from about 24 to about 48 grams per square meter and an apparent density of from about 0.10 to about 0.12 grams per cubic centimeter as made by the process described in U.S. Pat. No. 3,301,746 issued to Sanford and Sisson on Jan. 31, 1967 and which patent is hereby incorporated herein by reference has been found to be quite satisfactory for use as the absorbent element 56. Paper tissue made by the process described in U.S. Pat. No. 3,994,771 issued to Morgan et al. on Nov. 30, 1976, and which patent is hereby incorporated herein by reference, can also be used to good advantage as the absorbent element 56. Wet strength resins and latex binders can be, and preferably are, used to provide additional strength to the paper tissue used in the absorbent element 56.

The backsheet 54 of the secondary absorbent member 50 is preferably impervious to liquids (e.g., menses and/or urine) and is preferably manufactured from a thin plastic film, although other flexible liquid impervious materials may also be used. As used herein, the term "flexible" refers to materials which are compliant and will readily conform to the general shape and contours of the human body. In use, the backsheet 54 is interposed between the absorbent element 56 and the user's undergarments. The function of the backsheet 54 is to prevent exudates which may be expelled from or which inadvertently bypass the primary absorbent element and exudates absorbed and contained in the absorbent element 56 from contacting and soiling the user's undergarments. The backsheet 54 may thus comprise a woven or nonwoven material, polymeric films such as thermoplastic films of polyethylene or polypropylene, or composite materials such as a film-coated nonwoven material. Preferably, the backsheet is a polyethylene film having a thickness of from about 0.012 mm (0.5 mil) to about 0.015 mm (2.0 mil). Exemplary polyethylene films are manufactured by Clopay Corporation of Cincinnati, Ohio under the designation P18-0401 and by Ethyl Corporation, Visqueen Division, of Terre Haute, Ind., under the designation XP-39385. One suitable extensible backsheet is an extended adhesive film known as Formula #198-388 manufactured by the Findley Adhesives Company of Wauwatosa, Wis. The backsheet is preferably embossed and/or matte finished to provide a more clothlike appearance. Further, the backsheet may permit vapors to escape from the absorbent element 56 (i.e., breathable) while still preventing exudates from passing through the backsheet.

In preferred embodiments, the secondary absorbent member 50 is provided with a support means or attachment means, such as adhesive attachment means 58. The adhesive attachment means 58 provides a means for securing the compound sanitary napkin 20 in the crotch portion of the user's undergarment or panty. Thus, a portion or all of the outer or garment surface 55 of the backsheet 54 is coated with adhesive. In a preferred embodiment, at least a portion of the adhesive 58 is positioned on the garment surface 55 of the backsheet 54 adjacent the longitudinal side edges 21 of the secondary absorbent member 50. Any adhesive or glue used in the art for such purposes can be used for the adhesive herein, with pressure-sensitive adhesives being preferred. Suitable adhesives are Century A-305-IV manufactured by the Century Adhesives Corporation of Columbus, Ohio; and Instant Lock 34-2823 manufactured by the National Starch and Chemical Company of Bridgewater, N.J. Suitable adhesive fasteners are also described in U.S. Pat. No. 4,917,697.

The pressure-sensitive adhesive is typically covered with a removable release liner 59 in order to keep the adhesive from drying out or adhering to a surface other than the crotch portion of the panty prior to use. Suitable release liners are also described in the above referenced U.S. Pat. No. 4,917,697. Any commercially available release liners commonly used for such purposes can be utilized herein. Non-limiting examples of suitable release liners are BL30MG-A Silox El/O and BL30MG-A Silox 4P/O both of which are manufactured by the Akrosil Corporation of Menasha, Wis. The compound sanitary napkin 20 of the present invention is used by removing the release liner 50 and thereafter placing the sanitary napkin in a panty so that the adhesive 58 contacts the panty. The adhesive 58 maintains the sanitary napkin in its position within the panty during use.

The secondary absorbent member 50 may also have flaps which extend laterally from the side edge of the absorbent core 34. A number of sanitary napkins having flaps suitable or adaptable for use with the secondary absorbent member 50 of the compound sanitary napkin 20 of the present invention are disclosed in U.S. Pat. No. 4,687,478 issued to Van Tilburg on Aug. 18, 1987; U.S. Pat. No. 4,589,876 issued to Van Tilburg on May 20, 1986; and U.S. Pat No. 4,608,047 issued to Mattingly on Aug. 26, 1986. Each of these patents are incorporated herein by reference.

Optionally, the secondary absorbent member may comprise components that naturally wrap the sides of a wearer's panties. A sanitary napkin having components that naturally wrap the sides of a wearer's panties suitable for use with the secondary absorbent member of the compound sanitary napkin 20 of the present invention are disclosed in U.S. patent application Ser. No. 08/096,121, (P&G Case 4961) entitled "Absorbent Article having Panty Covering Components that Naturally Wrap the Sides of Panties", filed Jul. 22, 1993, in the names of Lavash, et al and U.S. patent application Ser. No. 08/277,733 (P&G Case 5354) entitled "Absorbent Articles Having Undergarment Covering Components with Zones of Extensibility", fried Jul. 20, 1994, in the names of Weinberger, et at. The disclosures of the preceding publications are incorporated herein by reference.

Referring now to FIG. 1, the secondary absorbent member 50 preferably has a length 60 and a width 61. The secondary absorbent member 50 is preferably from about 20 to 40 cm long, more preferably from about 25 to 35 cm long, and most preferably is about 30 cm long. The secondary absorbent member 50 is preferably from about 5 to 15 cm in width, more preferably from about 5 to 10 cm in width, and most preferably from about 5 to 8 cm in width. The thickness of the secondary absorbent member 50, as shown in cross-section in FIGS. 2 and 3, is generally somewhat less than its width.

The individual components of the primary absorbent member 30 and the secondary absorbent member 50 may be comprised of components that are extensible (preferably, capable of stretching) particularly in the longitudinal direction when the compound sanitary napkin is worn. Preferably, the compound sanitary napkin is capable of elongating in the longitudinal direction between about 15% and about 40% of its unstretched length. This extensibility provide better in-use fit, comfort, and decreased staining when the compound sanitary napkin is affixed to the wearer's undergarments. Sanitary napkins having extensible components are described in U.S. patent application Ser. Nos. 07/915,133 and 07/915,284 both filed Jul. 23, 1992, in the name of Osborn, et al. (PCT Publication Nos. WO 93/01785 and 93/01786, both published Feb. 4, 1993). The disclosures of the preceding publications are incorporated herein by reference.

In one preferred embodiment the primary absorbent member 30 and the secondary absorbent member 50 share a common length 65. The common length, refers to the length that the primary absorbent member 30 and the secondary absorbent member 50 have in common. However, it is quite possible for the secondary absorbent member to be somewhat longer than the primary absorbent member and still function effectively.

Preferably, the width of the secondary absorbent member 50 is at least 1.5 times the width of the primary absorbent member 30. More preferably, the width of the secondary absorbent member 50 is at least 2 times the width of said primary absorbent member 30. Most preferably, the width of the secondary absorbent member 50 is in the range from about 3 to about 8 times the width of the primary absorbent member 30.

To form the compound sanitary napkin of the present invention, the primary absorbent member 30 and the secondary absorbent member are joined by union means generally indicated as 70 in FIGS. 2 and 3. The precise nature of the union means is immaterial so long as the union means selected serves to join the primary absorbent member 30 and the secondary absorbent member 50 into the compound sanitary napkin 20 of the present invention with sufficient tenacity that the primary absorbent member 30 and the secondary absorbent member 50 are not disconnected during use. Union means such as adhesive attachment with well known hot melt and pressure sensitive adhesives are quite satisfactory. If the nature of the components selected to construct the constituents of the compound sanitary napkin 20 so permit, heat welding, ultrasonic welding, dynamic mechanical bonds or a combination of any of the above-mentioned means can be used.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A compound sanitary napkin comprising a primary absorbent member and a secondary member;

said primary absorbent member having a body facing side and a secondary absorbent member facing side, said primary absorbent member including an absorbent core and an outer cover, said body facing side defined as the side of said primary absorbent member which is most vertically opposed to said secondary absorbent member, said secondary absorbent member facing side defined as the side of said primary absorbent member which is juxtaposed said secondary absorbent member, said body facing side having a first width and said secondary absorbent member facing side having a second width, said first width being greater than said second width; and said secondary absorbent member having a primary absorbent member facing side, a garment facing side and a periphery defined by a pair of longitudinally extending edges and a pair of end edges, said secondary absorbent member comprising a liquid impervious backsheet, a liquid pervious topsheet joined directly with said backsheet in at least a portion of said periphery and an absorbent element positioned between said topsheet and said backsheet, said secondary absorbent member being joined with at least a portion of said secondary absorbent member facing side of said primary absorbent member, said longitudinal edges of said secondary absorbent member being disposed laterally outboard of said primary absorbent member such that said secondary absorbent member is wider than said primary absorbent member.

2. The compound sanitary napkin of claim 1 wherein said primary absorbent member comprises a containment layer.

3. The compound sanitary napkin of claim 1 wherein said primary absorbent member comprises an acquisition layer.

4. The compound sanitary napkin of claim 1 comprising a resilient member.

5. The compound sanitary napkin of claim 4 wherein said resilient member comprises a polyurethane foam.

6. The compound sanitary napkin of claim 1 wherein said primary absorbent member comprises a plurality of absorbent core members.

7. The compound sanitary napkin of claim 6 wherein said primary absorbent member comprises at least one first core member and at least one second core member, said second core member being compressible under normal wearing forces and said first core member being sufficiently resilient such that when subjected to normal wearing forces said first core member does not permanently collapse.

8. The compound sanitary napkin of claim 7 wherein said first core member is of generally arcuate cross-section.

9. The compound sanitary napkin of claim 7 wherein said first core member comprises a foam.

10. The compound sanitary napkin of claim 7 wherein said first core member is wrapped in a containment layer.

11. The compound sanitary napkin of claim 7 wherein said first core member is wrapped in an acquisition layer.

12. The compound sanitary napkin of claim 6 comprising a resilient member.

13. A compound sanitary napkin comprising a primary absorbent member and a secondary member;

said primary absorbent member having a body facing side and a secondary absorbent member facing side, said primary absorbent member including an absorbent core comprising at least one first core member, and at least one second core member; and an outer cover;

said body facing side defined as the side of said primary absorbent member which is most vertically opposed to said, secondary absorbent member, said secondary absorbent member facing side defined as the side of said primary absorbent member which is juxtaposed said secondary absorbent member, said body facing side having a first width and said secondary absorbent member facing side having a second width, said first width being greater than said second width; and said secondary absorbent member having a primary absorbent member facing side, a garment facing side and a periphery defined by a pair of longitudinally extending edges and a pair of end edges, said secondary absorbent member comprising a liquid impervious backsheet, a liquid pervious topsheet joined directly with said backsheet in at least a portion of said periphery and an absorbent element positioned between said topsheet and said backsheet, said secondary absorbent member being joined with at least a portion of said secondary absorbent member facing side of said primary absorbent member, said longitudinal edges of said secondary absorbent member being disposed laterally outboard of said primary absorbent member such that said secondary absorbent member is wider than said primary absorbent member.

14. The compound sanitary napkin of claim 13 wherein said second core member is compressible under normal wearing forces and said first core member is sufficiently resilient such that when subjected to normal wearing forces it does not permanently collapse.

15. The compound sanitary napkin of claim 13 wherein at least one of said first core members is generally in the shape of a parallelepiped.

16. The compound sanitary napkin of claim 13 wherein said first core members comprise a foam.

17. The compound sanitary napkin of claim 13 wherein said first core member comprises a different material than said second core member.

18. The compound sanitary napkin of claim 13 comprising a resilient member.

19. The compound sanitary napkin of claim 18 wherein said resilient member comprises a polyurethane foam.

* * * * *

UNITED STATES PATENT AND TRADEMARK OFFICE
CERTIFICATE OF CORRECTION

PATENT NO. : 5,695,324
DATED : December 9, 1997
INVENTOR(S) : David M. Weirich

It is certified that error appears in the above-identified patent and that said Letters Patent is hereby corrected as shown below:

Column 3,
Line 63, "longitudinal 14" should read -- longitudinally --.

Signed and Sealed this

Twenty-fifth Day of September, 2001

Attest:

NICHOLAS P. GODICI
Attesting Officer
Acting Director of the United States Patent and Trademark Office